United States Patent
Agarwal et al.

(10) Patent No.: US 9,522,230 B2
(45) Date of Patent: Dec. 20, 2016

(54) MECHANICAL LEECH SYSTEM

(71) Applicant: BioMime Innovations, LLC, Magna, UT (US)

(72) Inventors: Jayant Agarwal, Salt Lake City, UT (US); Scott Ho, Salt Lake City, UT (US); Jessica Kuhlman, South Jordan, UT (US); Andy Thompson, Magna, UT (US)

(73) Assignee: Biomime Innovations, LLC, Magna, UT (US)

( * ) Notice: Subject to any disclaimer, the term of this patent is extended or adjusted under 35 U.S.C. 154(b) by 281 days.

(21) Appl. No.: 14/249,320

(22) Filed: Apr. 9, 2014

(65) Prior Publication Data

US 2014/0309619 A1    Oct. 16, 2014

Related U.S. Application Data

(60) Provisional application No. 61/853,763, filed on Apr. 10, 2013.

(51) Int. Cl.
*A61M 5/158* (2006.01)
*A61M 1/00* (2006.01)

(52) U.S. Cl.
CPC ........... *A61M 5/158* (2013.01); *A61M 1/0023* (2013.01); *A61M 1/0001* (2013.01); *A61M 1/0066* (2013.01); *A61M 1/0084* (2013.01); *A61M 1/0088* (2013.01); *A61M 2005/1586* (2013.01); *A61M 2202/0478* (2013.01); *A61M 2206/11* (2013.01)

(58) Field of Classification Search
CPC ................ A61M 5/158; A61M 1/0023; A61M 2005/1586;A61M 2206/11; A61M 2202/0478; A61M 1/0066; A61M 1/0084; A61M 1/0001; A61M 5/3205; A61M 5/3295; A61M 37/0084; A61M 1/0088
USPC ........................................................ 604/506
See application file for complete search history.

(56) References Cited

U.S. PATENT DOCUMENTS

| 4,464,178 A * | 8/1984 | Dalton | A61M 39/0208 128/DIG. 26 |
| 6,007,495 A | 12/1999 | Matula | |
| 6,340,354 B1 | 1/2002 | Rambin | |
| 7,344,499 B1 * | 3/2008 | Prausnitz | A61B 5/1411 600/309 |

(Continued)

*Primary Examiner* — Imani Hayman
*Assistant Examiner* — Hamza Darb
(74) *Attorney, Agent, or Firm* — David W. Meibos; Maywood IP Law (57) ABSTRACT

A mechanical leech system may include a fluid exchange assembly. The fluid exchange assembly may be attached to a patient's target tissue area via suturing or the like, and may be activated to perform blood removal and treatment agent infusion. The fluid exchange assembly may include an inflow pathway for infusion of treatment agents into the tissue area, and an outflow pathway for removal of blood. The outflow pathway may be sized and/or shaped to promote laminar fluid flow and avoid coagulation. The assembly may include a channel housing, gasket, and base. Needles seated in the assembly may receive blood from a patient and infuse a treatment agent into the patient. The assembly may be connectable to a pump to urge the blood and the treatment agent through the inflow and outflow pathways. A cradle optionally provides protection and storage for the assembly.

19 Claims, 9 Drawing Sheets

(56) References Cited

U.S. PATENT DOCUMENTS

| | | | |
|---|---|---|---|
| 7,713,266 B2* | 5/2010 | Elkins | A61B 18/02 |
| | | | 606/20 |
| 2005/0033197 A1 | 2/2005 | Cottler | |
| 2009/0093754 A1* | 4/2009 | Hartig | A61M 1/0082 |
| | | | 604/28 |
| 2009/0157041 A1* | 6/2009 | Pettis | A61M 5/28 |
| | | | 604/506 |
| 2011/0306853 A1* | 12/2011 | Black | A61B 5/1468 |
| | | | 600/309 |
| 2013/0102954 A1* | 4/2013 | Choi | A61N 1/327 |
| | | | 604/21 |

* cited by examiner

MECHANICAL LEECH SYSTEM

CROSS-REFERENCE TO RELATED APPLICATIONS

The present application claims the benefit of U.S. Provisional Application Ser. No. 61/853,763, Attorney's Docket No. 0153EP.PROV, entitled MECHANICAL LEECH SYSTEM, which was filed on Apr. 10, 2013. The foregoing is incorporated by reference as though set forth herein in its entirety.

TECHNICAL FIELD

The present invention relates to medical devices to remove excess blood from tissue. More specifically, the present invention relates to a system and method capable of removal of blood and other body fluids, as well as infusion of materials into the body.

BACKGROUND

Oftentimes during surgery, tissue is sewn together to repair or reconstruct a defect. When the tissue is reconnected, the arteries and some of the veins are anastomosed or connected. During the healing phase, the arteries may supply blood to the repaired tissue faster than the veins can remove the blood. This can lead to pooling of blood in the repaired tissue and can cause local tissue congestion and necrosis.

Due to this problem, surgeons require a way to remove blood from the surgically repaired tissue. The current standard of practice is to use live leeches. The leeches attach to the tissue, supply a local anticoagulant, and remove blood. Although effective, the leeches can be difficult to maintain, store only a limited amount of blood and can cause infections. In addition, it is difficult to measurably and precisely control the fluid removal and the anticoagulant infusion provided by the leeches. For these reasons and others, there is a need for a device that can effectively, safely and reliably remove blood from surgically repaired tissues.

SUMMARY OF THE INVENTION

The various systems and methods of the present invention have been developed in response to the present state of the art, and in particular, in response to the problems and needs in the art that have not yet been fully solved by currently available technology. For example, the systems and methods of the present invention may provide a leeching and infusion assembly which promotes laminar flow of blood through the system, avoiding coagulation. Further the system provided is low profile and includes no moving parts, allowing a patient to comfortably and safely carry the assembly between fluid exchange procedures.

To achieve the foregoing, and in accordance with the invention as embodied and broadly described herein, one embodiment of the invention includes a system for promoting fluid exchange within a target tissue area. The system may include a first needle with a first lumen sized to receive blood from target tissue area, a second needle with a second lumen sized to receive blood from the target tissue area, and a housing. The housing may be shaped to define a first outflow channel with a first branch, a second branch, and an exit branch in fluid communication with the first branch and the second branch. The housing may also be shaped to define an outflow exit port in fluid communication with the exit branch, a first outflow entrance port in fluid communication with the first branch, and a second outflow entrance port spaced apart from the first outflow entrance port and in fluid communication with the second branch. The first and second needles may be coupled to the first outflow entrance port and the second outflow entrance port, respectively, such that blood flows from the first lumen into the first branch and from the second lumen into the second branch. The first outflow channel may be shaped to promote laminar flow of blood from the first and second outflow entrance ports to the outflow exit port.

The first branch may have, along a majority of its length, a first cross-sectional area. The second branch may have, along a majority of its length, a second cross-sectional area. The exit branch may have, along a majority of its length, an exit cross-sectional area. The first cross sectional area may be substantially equal to the second cross-sectional area and the exit cross-sectional area may be substantially equal to the sum of the first and second cross-sectional areas. The first branch and the second branch may be substantially equal in length. The first branch, the second branch, and the exit branch may cooperate to define a T-shape.

The system may further include a third needle with a third lumen. The housing may further have an inflow channel and an inflow exit port in fluid communication with the inflow channel. The third needle may be coupled to the inflow exit port to permit fluid to flow from the inflow channel into the third lumen.

The system may further include a fourth needle with a fourth lumen sized to receive blood from the target tissue area and a fifth needle with a fifth lumen sized to receive blood from the target tissue area. The housing may further include a second outflow channel with a second outflow channel first branch, a second outflow channel second branch, and a second outflow channel exit branch in fluid communication with the second outflow channel first branch and the second outflow channel second branch. The housing may further include a second outflow channel outflow exit port in fluid communication with the second outflow channel exit branch, a second outflow channel first outflow entrance port in fluid communication with the second outflow channel first branch, and a second outflow channel second outflow entrance port spaced apart from the second outflow channel first outflow entrance port and in fluid communication with the second outflow channel second branch. The fourth and fifth needles may be coupled to the second outflow channel first outflow entrance port and the second outflow channel second outflow entrance port, respectively, such that blood flows from the fourth lumen into the second outflow channel first branch and from the fifth lumen into the second outflow channel second branch. The second outflow channel may be shaped to promote laminar flow of blood from the second outflow channel first outflow entrance port and the second outflow channel second outflow entrance port to the second outflow channel outflow exit port.

The housing may further include at least one securement opening sized to receive a suture to secure the housing to the target tissue area. The system may further include a cradle shaped to retain the housing; the cradle may have a plurality of openings sized to receive the first and second needles.

The housing may include a channel housing coupled to a base. The channel housing may have the first outflow channel, and the base may have the first outflow entrance port, the second outflow entrance port, and the outflow exit port. The system may further have a gasket positioned between the channel housing and the base to restrict fluid leakage from the first outflow channel.

In one embodiment of the invention, a system for promoting fluid exchange within a target tissue area may have a first needle with a first lumen sized to receive blood from target tissue area; a second needle with a second lumen sized to receive blood from the target tissue area; and a housing with a first outflow channel, an outflow exit port in fluid communication with the first outflow channel, a first outflow entrance port in fluid communication with the first outflow channel, and a second outflow entrance port spaced apart from the first outflow entrance port and in fluid communication with the first outflow channel. The first and second needles may be coupled to the first outflow entrance port and the second outflow entrance port, respectively, such that blood flows from the first lumen into the first outflow channel and from the second lumen into the first outflow channel. The outflow exit port may be adapted to be connected to an external pump, and the housing may contain no moving parts.

The system may further have a third needle with a third lumen. The housing may further have an inflow channel and an inflow exit port in communication with the inflow channel. The third needle may be coupled to the inflow exit port to permit fluid to flow from the inflow channel into the third lumen.

The system may further have a fourth needle with a fourth lumen sized to receive blood from the target tissue area and a fifth needle with a fifth lumen sized to receive blood from the target tissue area. The housing may further have a second outflow channel, a second outflow channel outflow exit port in fluid communication with the second outflow channel, a second outflow channel first outflow entrance port in fluid communication with the second outflow channel, and a second outflow channel second outflow entrance port spaced apart from the second outflow channel first outflow entrance port and in fluid communication with the second outflow channel. The fourth and fifth needles may be coupled to the second outflow channel first outflow entrance port and the second outflow channel second outflow entrance port, respectively, such that blood flows from the fourth lumen into the second outflow channel and from the fifth lumen into the second outflow channel.

The first outflow channel may have a first branch, a second branch, and an exit branch. The first outflow channel may be shaped to promote laminar flow of blood through the first outflow channel. The housing may include a channel housing coupled to a base. The channel housing may have the first outflow channel, and the base may have the first outflow entrance port, the second outflow entrance port, and the outflow exit port.

In one embodiment, the invention may include a method for promoting fluid exchange within a target tissue area. The method may include penetrating the target tissue area with a first needle, a second needle, and a third needle seated in a housing. The method may further include, from outside the housing, exerting pressure on blood to draw the blood from the target tissue area through the first needle and the second needle into the housing. The method may further include conducting the blood from the first and second needles into a first outflow channel in the housing, and conducting the blood out of the housing through a first outflow exit port. The method may further include, from outside the housing, exerting pressure on a treatment agent to urge the treatment agent to flow into an inflow channel in the housing. The treatment agent may flow through a first inflow entrance port into the inflow channel. The method may further include conducting the treatment agent through an inflow exit port and into the third needle, and conducting the treatment agent from the third needle into the target tissue area.

Drawing the blood from the target tissue area and urging the treatment agent into the inflow channel may be carried out simultaneously. The method may further include attaching the housing to the target tissue area by passing a suture through a securement opening of the housing and securing the suture to the target tissue area.

The method may further include connecting the first outflow exit port and the first inflow entrance port to a pump external to the housing, and activating the pump to exert the pressure on the blood and exert the pressure on the treatment agent. The method may further include penetrating the target tissue area with a fourth needle and a fifth needle seated in the housing. The method may further include, from outside the housing, exerting pressure on the blood to draw the blood from the target tissue area through the fourth needle and the fifth needle into the housing, and conducting the blood out of the housing through a second outflow exit port.

These and other features and advantages of the present invention will become more fully apparent from the following description and appended claims, or may be learned by the practice of the invention as set forth hereinafter.

BRIEF DESCRIPTION OF THE DRAWINGS

Exemplary embodiments of the invention will become more fully apparent from the following description and appended claims, taken in conjunction with the accompanying drawings. Understanding that these drawings depict only exemplary embodiments and are, therefore, not to be considered limiting of the invention's scope, the exemplary embodiments of the invention will be described with additional specificity and detail through use of the accompanying drawings in which:

DETAILED DESCRIPTION

Exemplary embodiments of the invention will be best understood by reference to the drawings, wherein like parts are designated by like numerals throughout. It will be readily understood that the components of the invention, as generally described and illustrated in the Figures herein, could be arranged and designed in a wide variety of different configurations. Thus, the following more detailed description of the embodiments of the apparatus, system, and method, as represented in FIGS. 1 through 9, is not intended to limit the scope of the invention, as claimed, but is merely representative of exemplary embodiments of the invention.

The phrases "connected to," "coupled to" and "in fluid communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1:
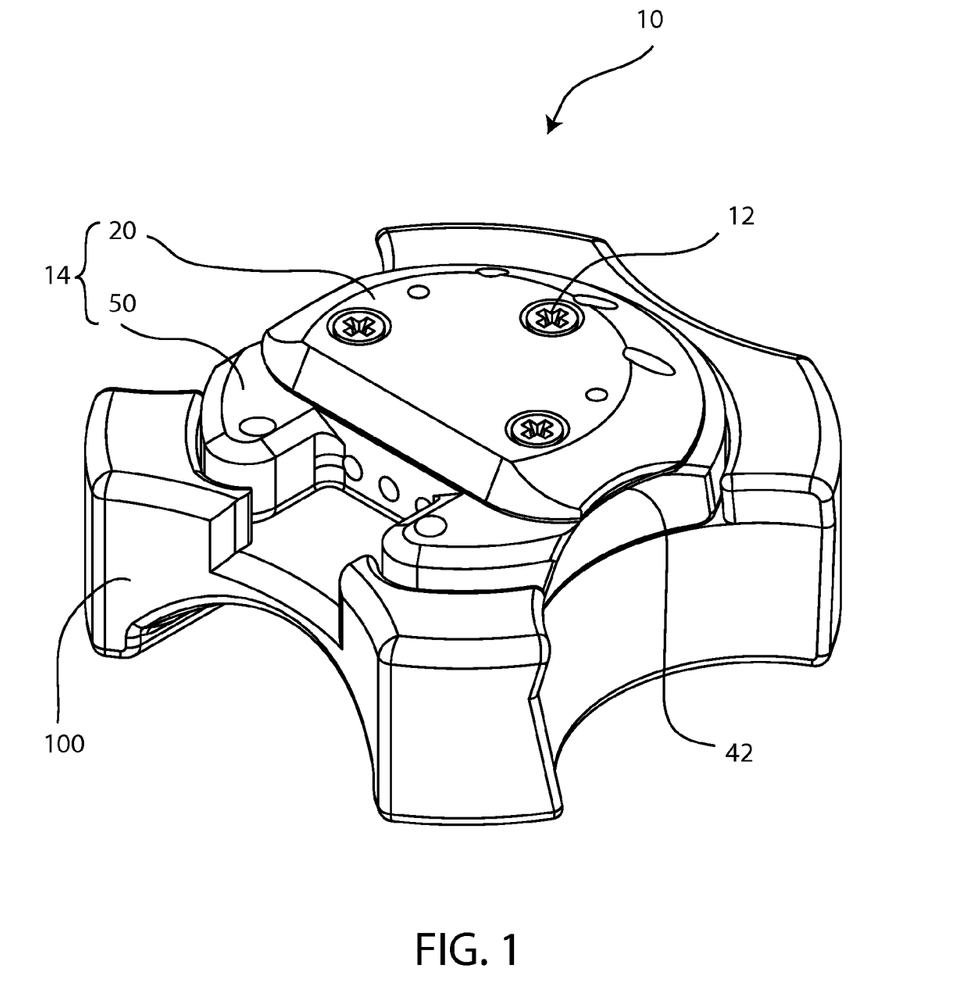
FIG. 1 is an isometric view of a mechanical leech system according to one embodiment of the invention.
Figure 2:
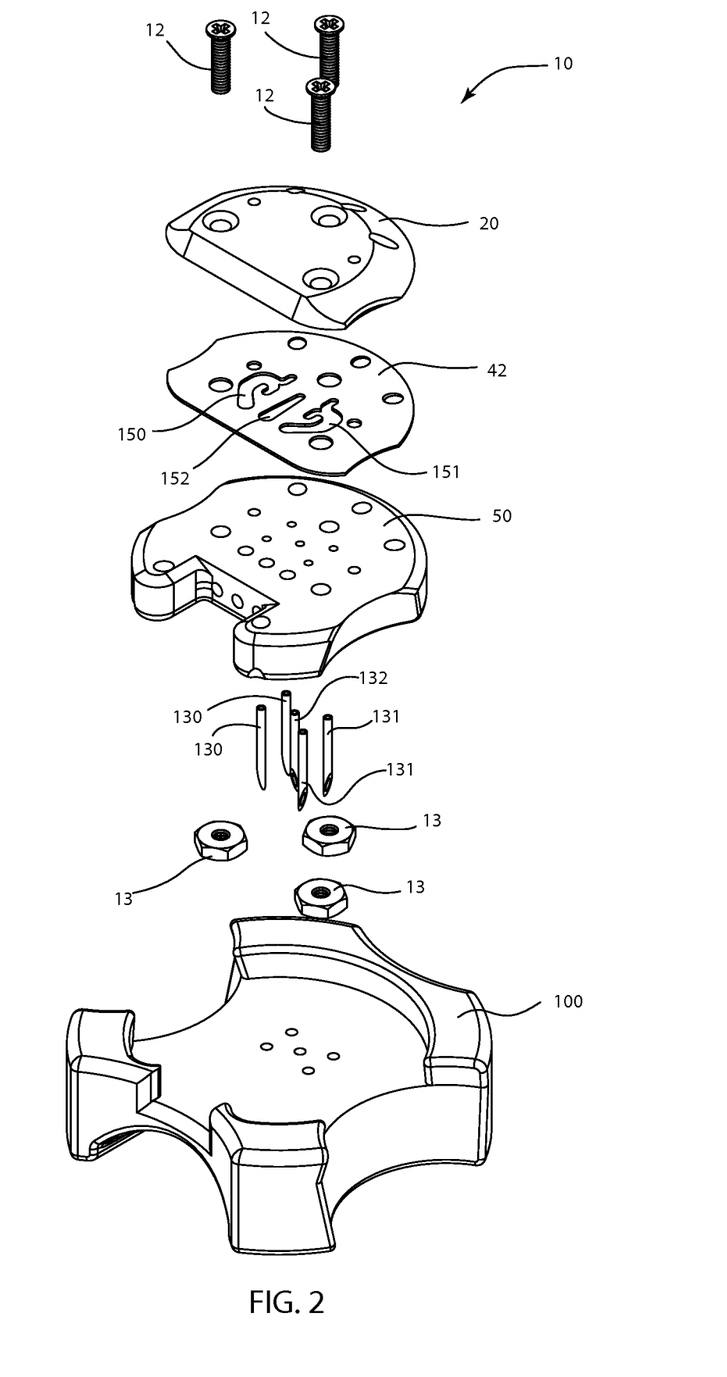
FIG. 2 is an exploded view of the mechanical leech system of FIG. 1 and inflow.
Figure 7A:
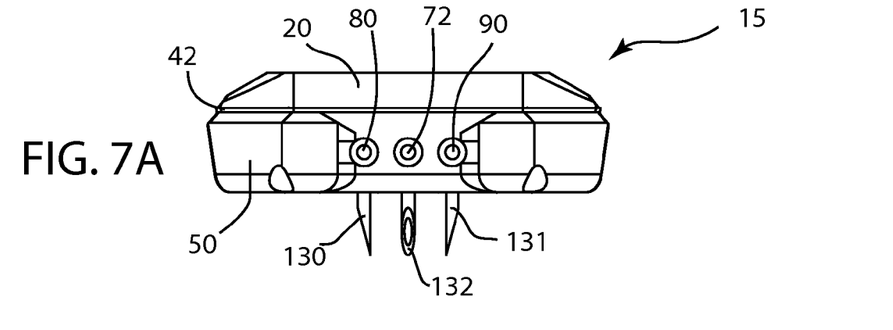
FIGS. 7A, 7B, and 7C are front, top, and side cross-sectional views, respectively, of a fluid exchange assembly of the mechanical leech system of FIG. 1.

Referring to FIGS. 1 and 2, isometric views illustrate a mechanical leech system, or system 10, according to one embodiment of the invention. The system 10 may include a channel housing 20, a base 50 and a cradle 100. With reference also to FIG. 7A, a plurality of needles 130, 131, 132 may project from the base 50 toward the cradle 100. A membrane 42 may be provided to act as a gasket between the base 50 and the channel housing 20, and may be formed of an elastomer such as silicone or silicone rubber. When the system 10 is in storage or is undergoing sanitization or sterilization, the channel housing 20 and base 50 may be assembled to rest in the cradle 100, as seen in FIG. 1. The channel housing 20 and the base 50 may be assembled with the cradle 100 in a snap fit, press fit, or other type of engagement wherein the cradle 100 retains the channel housing 20 and the base to protect the needles 130, 131, 132. During use of the system 10 for fluid removal and/or infusion, the cradle 100 may be detached and set aside while channel housing 20 and the base 50 are engaged in fluid exchange.

The channel housing 20 and the base 50 together constitute a housing 14. One or more fasteners 12 secured with nuts 13 may attach the channel housing 20 to the base 50. In other embodiments of the invention, the housing 14 may be formed monolithically as a single piece, or may be formed of two or more pieces shaped differently from the channel housing 20 and the base 50. The channel housing 20, the membrane 42, the base 50 and the needles 130, 131, 132 define a fluid exchange assembly 15, which may be operable for fluid removal and/or infusion independently of the cradle 100.

Figure 7B:
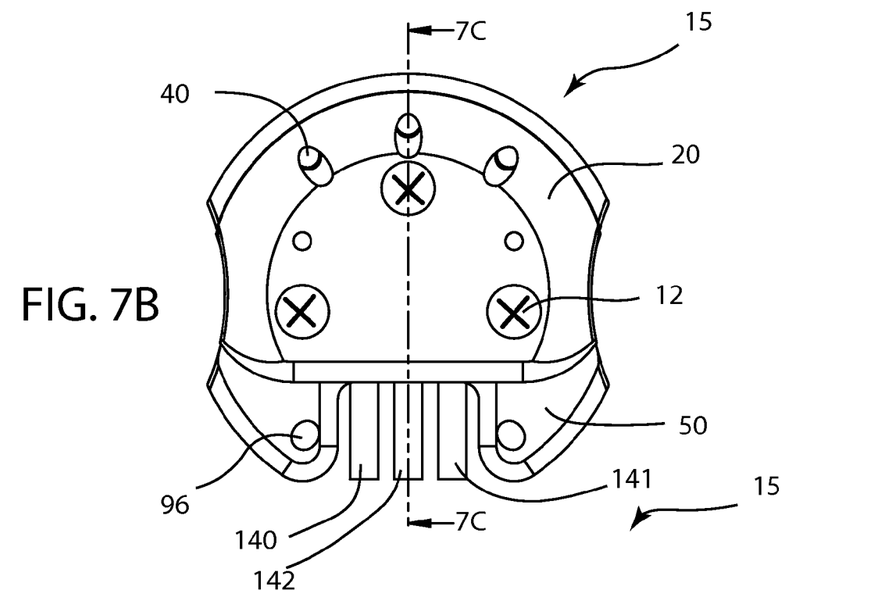
Figure 7C:
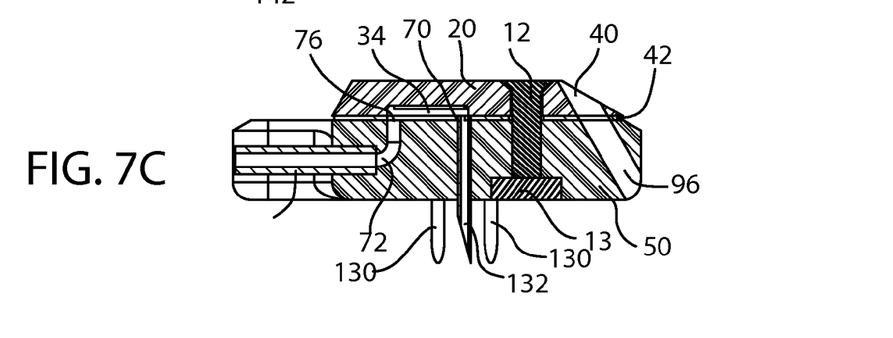

Via attachable outflow tubes 140, 141 and an inflow tube 142, seen in FIGS. 7A-7C, the system 10 may be engaged with a peristaltic pump or other pump to simultaneously pump an anticoagulant into a treatment area on a patient, and remove blood and other fluids from the treatment area. Notably, infusion and fluid removal need not be simultaneous, and may be performed in any sequence including alternating, simultaneous, or other sequences. Alternatively, the system 10 may be used to perform only infusion or fluid removal, without performing the other. Notably, only the ends of the inflow and outflow tubes 140, 141, 142 are shown in FIGS. 7A-7C. The inflow and outflow tubes 140, 141, 142 may be flexible tubing provided at any length necessary to connect to the housing 14 to a pump, treatment fluid reservoir, blood reservoir, and/or any other component that may be desirable included as part of the system 10.

The inflow and outflow tubes 140, 141, 142 may be coupled to the housing 14 in a wide variety of ways, including but not limited to mechanical fasteners, interference fit systems, adhesive bonding, chemical bonding, and the like. In one embodiment, standardized fluid interlock systems for connecting surgical tubing may be integrated into the housing 14 to facilitate the attachment of the inflow and outflow tubes 140, 141, 142 to the housing 14.

Throughout the description of the system 10, the term "inflow" is used to identify portions or components of a pathway routed through the system 10 to convey fluid toward a treatment area. For example, heparin may be introduced along an inflow pathway through the fluid exchange assembly 15 into targeted tissue on a patient. The term "outflow" is used to identify portions or components of a pathway in the system 10 that conveys fluid out of a treatment area and through the system 10. For example, blood may flow out of the targeted tissue along an outflow pathway through the fluid exchange assembly 15.

Referring to FIGS. 3A-3E, the channel housing 20 may include a channel housing body 22, which may be generally semicircular and flat in shape. In other embodiments, the channel housing body may be circular, oval, rectangular, asymmetrical, elongated or have any other shape.

Figures 3A, 3B, 3C, 3D, 3E:
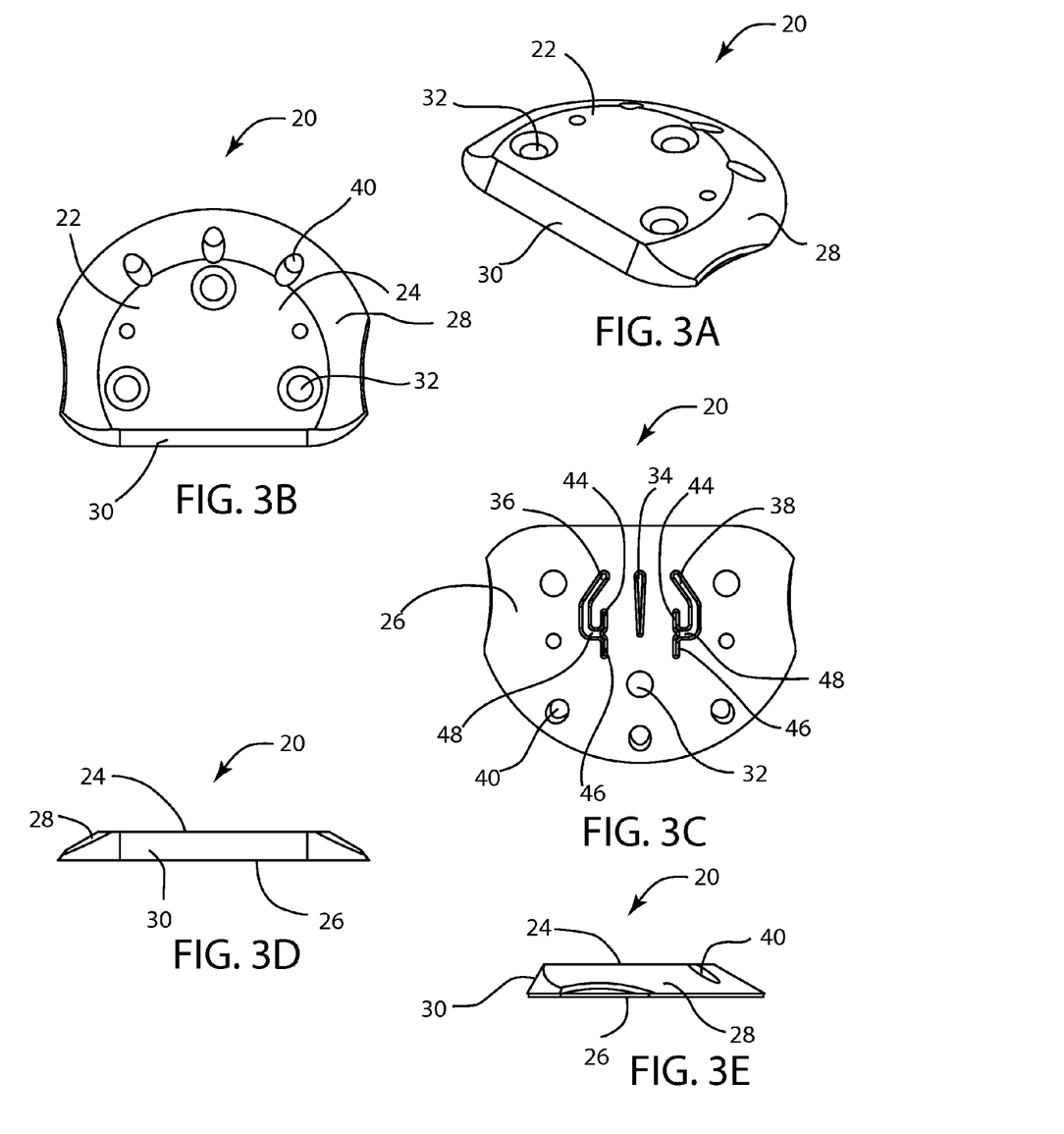
FIGS. 3A, 3B, 3C, 3D, and 3E are a perspective view, a top view, a bottom view, a front view, and a side view, respectively, of the channel housing of FIG. 1.

Returning to FIGS. 3A-3E, the channel housing 20 may include a top side or first side 24, which may face in a direction generally opposite to that of a bottom side, or second side 26. A curved beveled edge 28 may connect a portion of the periphery of the first side 24 with a portion of the periphery of the second side 26. A straight, slanted edge 30 may connect the remainder of the peripheries of the first and second sides 24, 26 together. Each of the first and second sides 24, 26 may be flat or planar as seen in FIGS. 3D and 3E. A plurality of fastener openings 32 may extend through the channel housing body 22, between and in fluid communication with the first and second sides 24, 26. The fastener openings 32 may be countersunk and may include threading, grooves or other features for engagement with screw shafts, nuts or other fasteners. The countersink may enable the top surfaces of the fasteners 12 to lie flush with the first side 24 when the fasteners 12 are used to attach the channel housing 20 to the channel base 50.

Figure 4:
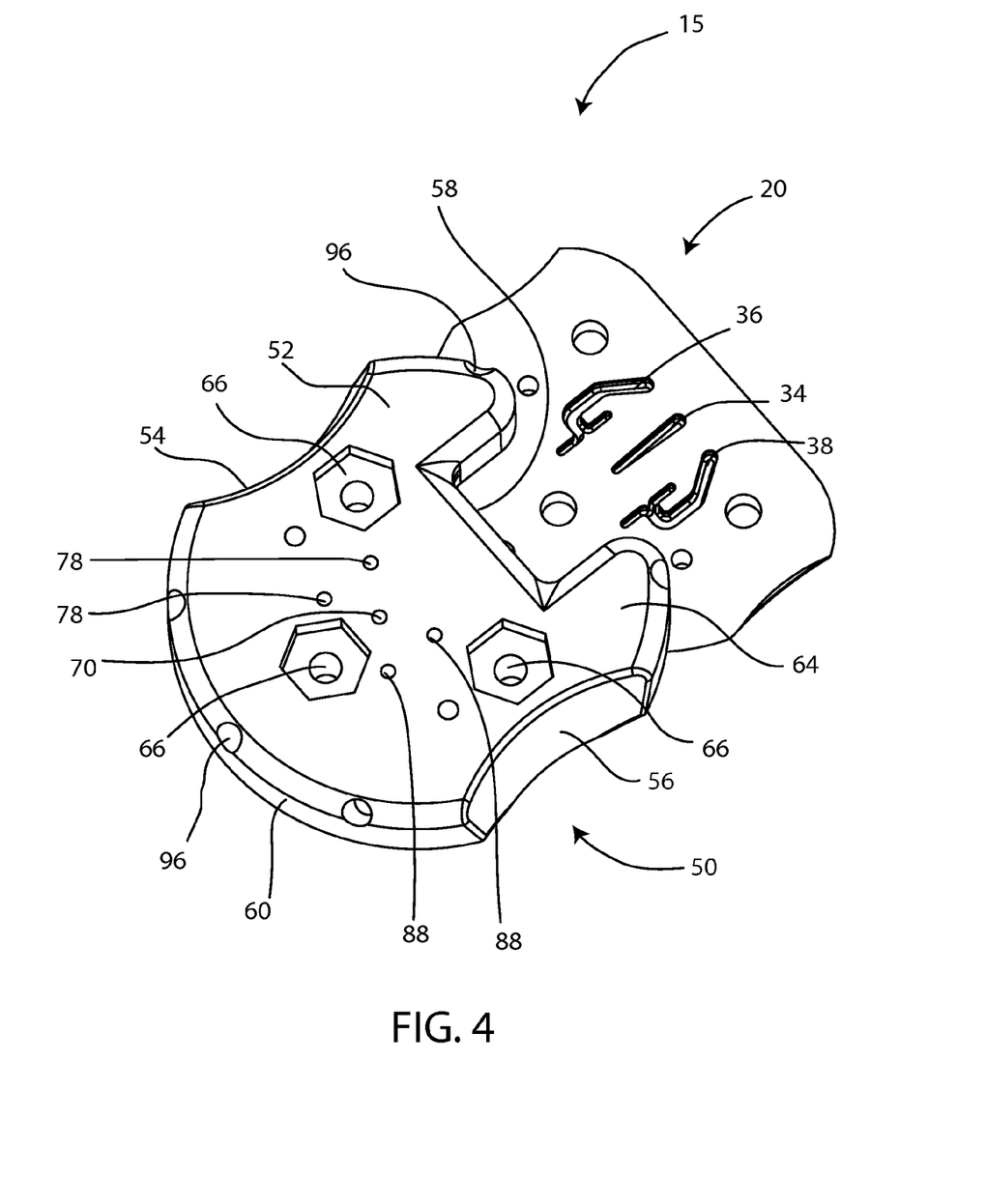
FIG. 4 is a partially exploded view of the channel housing and the base of FIG. 1.
Figures 5A, 5B, 5C, 5D:
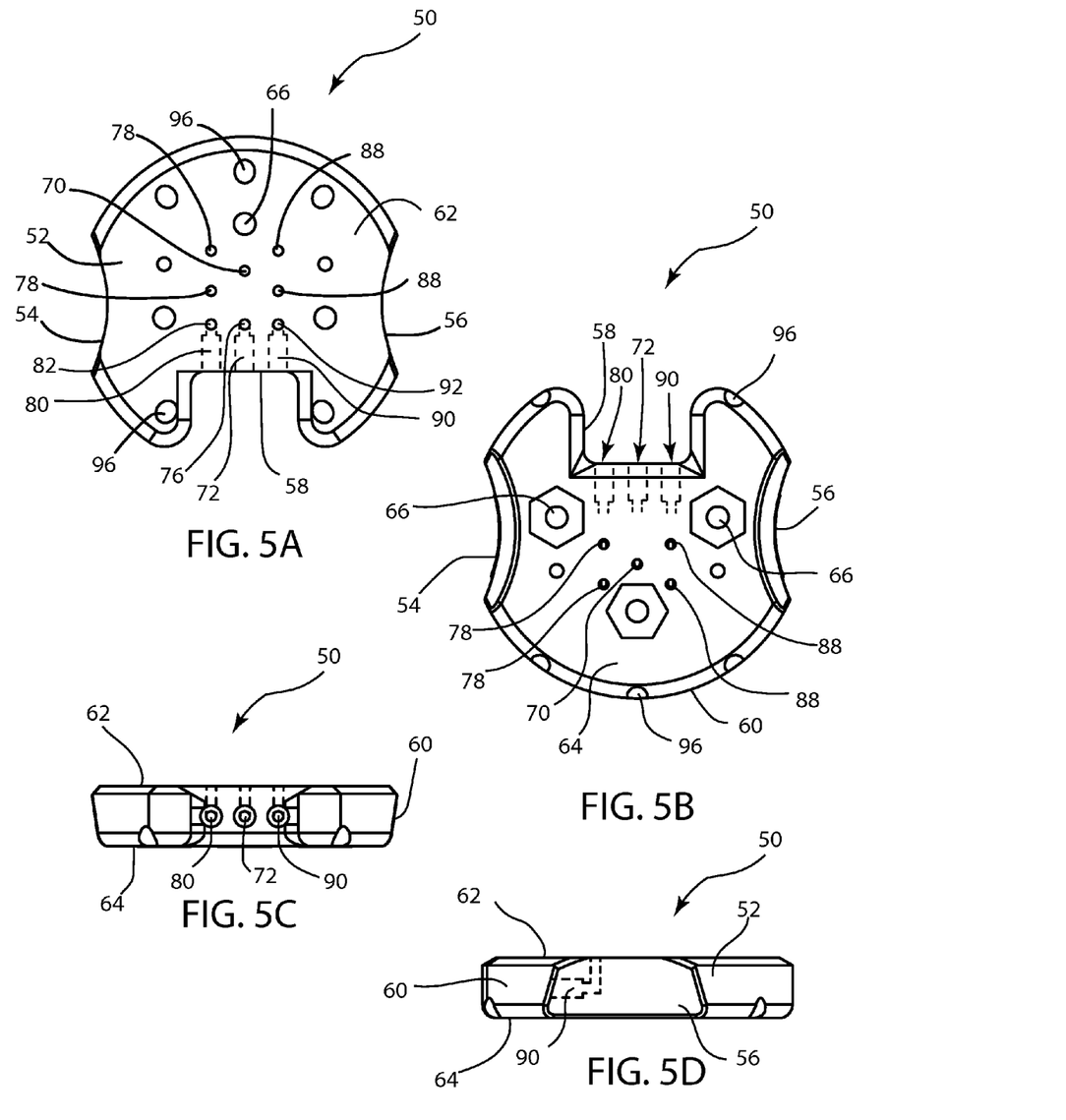
FIGS. 5A, 5B, 5C, and 5D are top, bottom, front, and side views, respectively, of the base of FIG. 1.

Referring to FIGS. 3C and 4, several channels may be recessed into the channel housing body 22 from the bottom or second side 26. An inflow channel 34 may be located generally along a midline of the channel housing body 22, between a first outflow channel 36 and a second outflow channel 38. Those of skill in the art will appreciate that the number, position, and configuration of the channels in the channel housing body 22 may vary. The channels 34, 36, 38 may be blind channels in that they may not open out onto the first side 24 of the channel housing body 22. The channels 34, 36, 38 may include smooth, curved walls that promote laminar fluid flow and avoid pooling, stagnation and/or coagulation of blood and/or other fluids. Each of the outflow channels 36, 38 may include multiple branches, which may include a first branch 44 and a second branch 46 which may be termed entrance branches, and a third branch 48 which may termed an exit branch. Each first branch 44 has a length $L_{44}$ which may be equal to a length $L_{46}$ of each second branch, and the exit branch has a length $L_{48}$. The first and second branches 44, 46 may converge at and supply fluid to the exit branch 48. Thus, regardless of whether fluid enters an outflow channel 36 or 38 through the first branch 44 or through the second brand 46, the length the fluid must flow through the channel 36 or 38 may be the same ($L_{44}$+$L_{48}$=$L_{46}$+$L_{48}$). This relationship may encourage laminar flow of blood through the outflow channels 36, 38 by equalizing head loss between the branches as blood flows into the entrance branches (i.e., the branches 44, 46) and out of the exit branch (i.e., the branch 48).

In the embodiment shown, the cross-sectional area, normal to fluid flow, of the exit branch 48 may be twice the cross-sectional area of each of the branches 44, 46 that serve as entrance branches. In other words, the cross-sectional area of the exit branch 48 may be equal to the sum of the cross-sectional areas of the two entrance branches 44, 46 that feed into the exit branch 48. This relationship may encourage laminar flow of blood and/or other fluids through the outflow channels 36, 38 by maintaining a constant flow velocity through each outflow channel 36, 38.

In the embodiment shown, each outflow channel 36, 38 has a T-shape formed by its first branch 44, second branch 46, and exit branch 48. The first and second branches are coaxially aligned along a first axis, which is substantially perpendicular to a second axis formed by the exit branch. It is appreciated that in other embodiments of the invention, each outflow channel may take a different shape. For example, in other embodiments the first and second branches may not be coaxially aligned, and/or may not be perpendicular to the exit branch. In other embodiments, more or fewer branches may be included per channel.

The channel housing 20 may further include one or more securement passages 40. Each securement passage 40 may pass through the channel housing body 22 and may provide a passage through which one or more sutures, lines or other fasteners may be threaded to secure the channel housing 20 to the base 50 and/or to a patient. The securement passages 40 may be angled as seen in FIGS. 2, 3A and 3B to avoid cutting or wear on sutures deployed in the passages. The shape of the securement passages 40 and/or the corresponding openings may also help avoid tearing of skin or tissues to which the housing is secured.

Referring to FIGS. 4 and 5A-5D, the base 50 may also be referred to as a channel base. The base 50 as depicted in the figures may include a base body 52 which is generally circular, with finger grips 54, 56 and a notch 58 incised into an outer perimeter wall 60 of the base. In other embodiments of the invention, the shape of the base 50 may be circular, oval, rectangular, asymmetrical, elongated or any other shape. The shape of the base may generally match the shape of the channel housing as shown; in other embodiments the base and channel housing may differ in shape from one another. The base 50 may include a top side, or first side 62 which may face a direction opposite to that of a bottom side, or second side 64. The second side 64 may be flat as shown but in other embodiments may be ridged, curved, concave, or convex in order to best complement the surface of the skin or tissue to which it may be attached. Several fastener openings 66 may extend through the base body 52, between and in fluid communication with the first and second sides 62, 64. The fastener openings 66 may be countersunk and may include threading, grooves or other features for engagement with screw shafts, nuts and/or other fasteners. When the channel housing 20 and the base 50 are properly assembled for use as in FIGS. 1 and 7A-C, the fastener openings 32 of the channel housing 20 may axially align with the fastener openings 66 of the base 50 to receive one or more fasteners such as a lines or screws (such as the fasteners 12) to fasten the channel housing 20 and channel base 50 together.

Figure 8A:
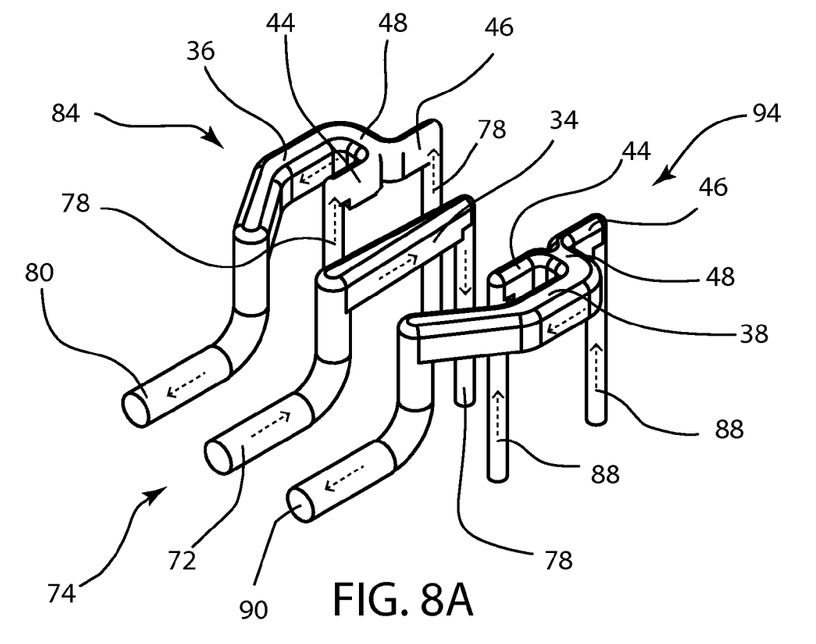
FIGS. 8A and 8B are top isometric and bottom isometric views, respectively, of inflow and outflow paths of the mechanical leech system of FIG. 1 with dashed lines showing the direction of fluid flow through the pathways.
Figure 8B:
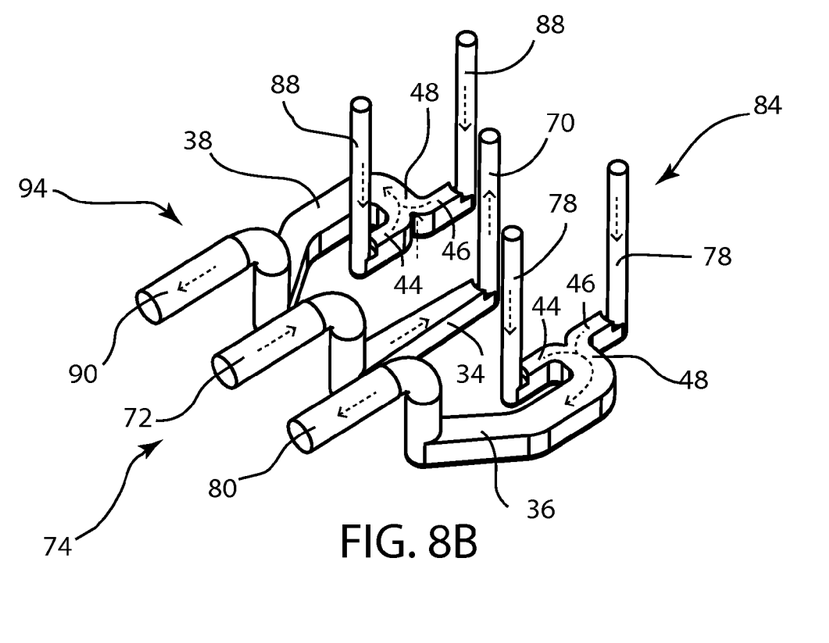

An inflow exit port 70 may be generally centered on the base body 52, and may extend between and in fluid communication with the first side 62 and the second side 64. An inflow entrance passage 72 may extend from the outer perimeter wall 60 within the notch 58 to an inflow entrance port 76 on the first side 62 of the base body 52. When the channel housing 20 and the base 50 are properly assembled for use as in FIGS. 1 and 7A-C, the inflow exit port 70 may abut and may be in fluid communication with the inflow channel 34, and the inflow entrance port 76 may also abut and be in fluid communication with the inflow channel 34. The inflow exit port 70 and inflow entrance port 76 may abut the inflow channel at separate locations on the inflow channel 34. With reference also to FIGS. 8A and 8B, the inflow tube 142 may be connected to the inflow entrance passage 72, and a fluid such as heparin may pass through the outflow tube 142, through the inflow entrance passage 72, out the inflow entrance port 76 into the inflow channel 34, along the inflow channel 34, into the inflow exit port 70, through the needle 132 lumen and into the tissue. The inflow entrance passage 72, inflow entrance port 76, inflow channel 34, inflow exit port 70, and the needle 132 lumen may define an inflow pathway 74. The membrane 42 may seal the interface between the second side 26 of the channel housing 20 and the first side 62 of the base 50, preventing unintentional leakage of heparin or other fluids out of the inflow pathway.

A set of first outflow entrance ports 78 may extend through base 50 between and in fluid communication with the first side 62 and the second side 64. A first outflow exit passage 80 may extend from a first outflow exit port 82 on the first side 62 of the base body 52 to the outer perimeter wall 60 within the notch 58. When the channel housing 20 and the base 50 are properly assembled for use as in FIGS. 1 and 7A-7C, each of the first outflow entrance ports 78 may abut and be in fluid communication with one of the branches 44, 46 of first outflow channel 36. Similarly, the first outflow exit port 82 may abut and be in fluid communication with the exit branch 48 of outflow channel 36. The first outflow entrance ports 78 and the first outflow exit port 82 may abut the outflow channel 36 at separate locations on the outflow channel 36. Each entrance port 78 may be equidistant from the exit port 82. In other embodiments, more than two entrance ports may feed into a given branch and/or channel.

In use, fluid exchange assembly 15 may be attached to tissue to be treated with the needles 130, 131, 132 penetrating the tissue, and the outflow tube 140 may be connected to the outflow exit passage 80. Blood and/or other fluids may pass into the needles 130 and through the first outflow entrance ports 78 to enter the first outflow channel 36. The blood and/or other fluid may then pass through the first and second branches 44, 46, into the exit branch 48 of the outflow channel 36, and out of the first outflow channel 36, through the first outflow exit port 82, along first outflow exit passage 80, and out into the tube connected thereto. The needles 130, first outflow entrance ports 78, first outflow channel 36, first outflow exit port 82, first outflow exit passage 80, and the tube connected thereto may cooperate to define a first outflow pathway 84.

A set of second outflow entrance ports 88 may extend through base 50 between and in fluid communication with the first side 62 and the second side 64. A second outflow exit passage 90 may extend from a second outflow exit port 92 on the first side 62 of the base body 52 to the outer perimeter wall 60 within the notch 58. When the channel housing 20 and the base 50 are properly assembled for use as in FIGS. 1 and 7A-7C, each of the second outflow entrance ports 88 may abut and be in fluid communication with one of the branches 44, 46 of second outflow channel 38, and the second outflow exit port 92 may abut and be in fluid communication with the exit branch 48 of outflow channel 38. The second outflow entrance ports 88 and the second outflow exit port 92 may abut the outflow channel 38 at separate locations on the outflow channel 38. Each entrance port 88 may be equidistant from the exit port 92. The inflow exit port 70 may be centered relative to the outflow entrance port(s) 78, 88. This arrangement may allow heparin or another material to be uniformly or evenly dispersed relative to the outflow entrance ports.

In use, with the fluid exchange assembly 15 is attached to tissue to be treated with the needles 130, 131, 132 penetrating the tissue as described above, and the outflow tube 141 may be connected to outflow exit passage 90. Blood and/or other fluids may pass into the needles 131 and through second outflow entrance ports 88 to enter second outflow channel 38. The blood and/or other fluid may then pass through first and second branches 44, 46, into the exit branch 48 of the outflow channel 38, and out of the second outflow channel 38, through the second outflow exit port 92, along second outflow exit passage 90, and out into the tube connected thereto. The needles 131, second outflow entrance ports 88, second outflow channel 38, second outflow exit port 92, second outflow exit passage 90, and the tube connected thereto may cooperate to define a second outflow pathway 94.

The base 50 may further include one or more securement passages 96. Each securement passage 96 may pass through the base body 52 and provides a passage through which a suture, line or other fastener may be threaded to secure the base 50 to the channel housing 20 and/or to a patient. One or more of the securement passages 96 may align in fluid communication with one or more securement passages 40 of the channel housing 20 when the housing 14 is properly assembled. Like the securement passages 40 on the channel housing 20, the base securement passages 96 may be optimally shaped to avoid wear or tearing of sutures and/or avoid tearing or damage to skin or tissues to which the base 50 is secured.

Referring to FIG. 2, the membrane 42 may include cutouts which have the same shapes as the inflow channel 34, the outflow channels 36, 38, the fastener openings 66 and the securement passages 40 of the channel housing 20. The outflow channel cutouts 150, 151 may be shaped like the outflow channels 38, 36, and the inflow channel cutout 152 may be shaped like the inflow channel 34. When sandwiched between the channel housing 20 and the base 50 as in FIG. 1, the membrane 42 may seal the interface between the second side 26 of the channel housing 20 and the first side 62 of the base 50, preventing unintentional leakage of blood or other fluids out of the inflow and outflow pathways 74, 84, 94. The membrane 42 and the first side 62 of the base 50 may also abut and close off the inflow channel 34 and the outflow channels 36, 38 between the port connections with the channels.

As seen in FIGS. 2 and 7, when the needles 130, 131 and 132 are seated in the ports 70, 78, 88 of the base 50, the needles 130, 131, 132 may project out of the second side 64 of the base 50. Each of the needles 130, 131, 132 may be hollow throughout, and may have a lumen through which fluid may pass, and may have a sharp tip with a slanted or beveled opening for optimum piercing ability. The inflow needle 132 may project from the inflow exit port 70. The outflow needles 130 may project from the outflow entrance ports 78, and the outflow needles 131 may project from the outflow entrance ports 88. The inflow and outflow needles 130, 131, 132 may be identically formed and sized; alternatively, they may vary in size if desired. For example, it may be advantageous to have the inflow needle 132 have a lumen that is larger or smaller in cross-sectional area than the sum of the cross-sectional areas of the lumens of the outflow needles 130, 131 in order to generate a desired ratio of fluid inflow to outflow. The lengths of the needles 130, 131, 132 may also vary.

Referring to FIGS. 6A-6D, the cradle 100 may include a cradle body 102 having a first side 104 and a second side 106. An outer wall 108 may form the outer perimeter of the cradle 100. The outer wall 108 may be indented in one or more locations; in other embodiments the outer wall may not include indentations. Two indentations of the outer wall 108 may serve as finger grips 110, 112. A notch 114 may be formed in a portion of the outer wall 108, separated from and between the finger grips 112. The notch 114 may allow space for ingress and egress of tubes or other elements connected to or associated with the fluid exchange assembly 15. The overall outer diameter of the cradle 100 may be greater than the outer diameter of the housing 14, to provide protection to the housing 14 during transport or storage.

Figure 6A:
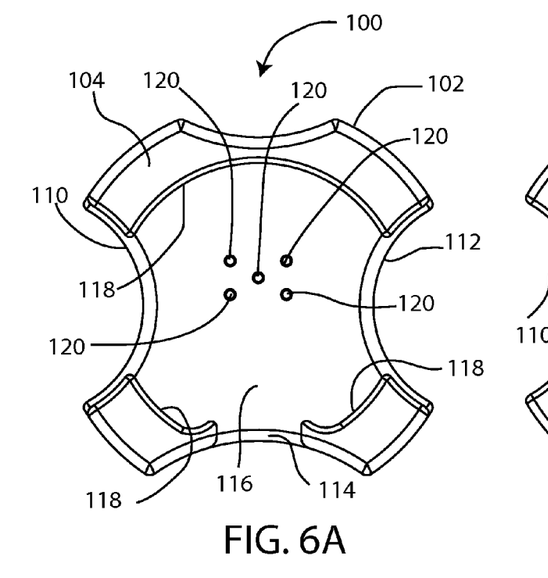
FIGS. 6A, 6B, 6C, and 6D are top, bottom, front, and side views, respectively, of the cradle of FIG. 1.
Figure 6B:
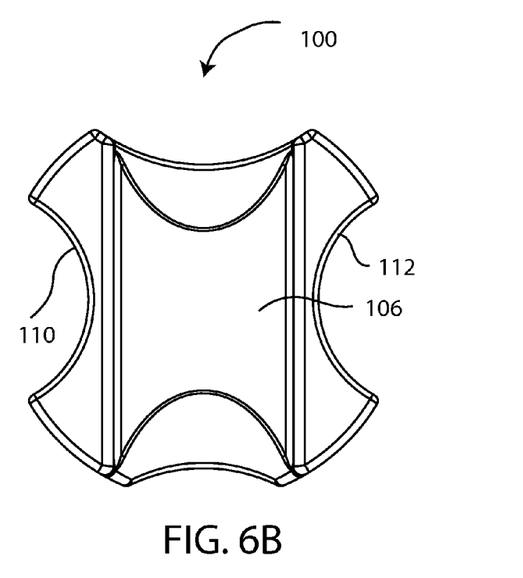
Figure 6C:
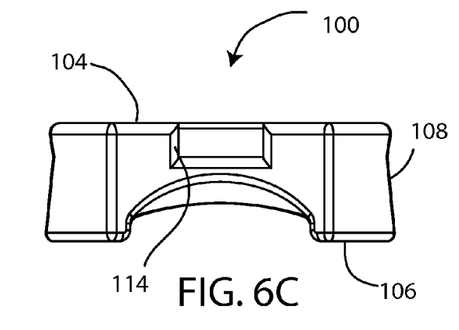
Figure 6D:
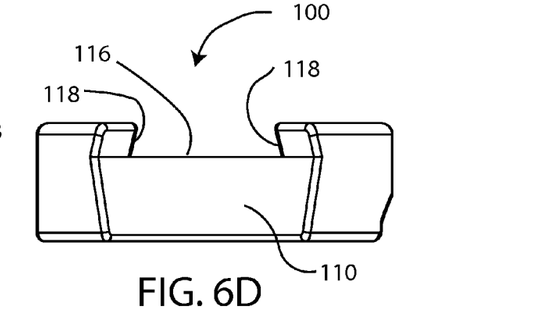

The first side 104 of the cradle 100 may include a platform 116 that is recessed into the cradle body 102. A rim 118 may be formed around the platform 116 and may project above it. The rim 118 may be angled, as best seen in FIG. 6D, to allow the base 50 to fit into the cradle 100 in a snap or press fit connection, as seen in FIG. 1. The angle between the rim 118 and the platform 116 may be less than 90 to provide retention of the base 50 within the cradle 100. The rim 118 may be discontinuous relative to the platform 116, as seen in FIG. 6B.

The platform 116 may include one or more cradle needle holes 120, which may be distributed in an arrangement that complements the arrangement of needles projecting from the fluid exchange assembly 15. When the system 10 is assembled as in FIG. 1, the needles 130, 131, 132 may project downward from the ports in the fluid exchange assembly 15, and are retained in the cradle needle holes 120. The cradle needle holes 120 may be deeper than the length of any needles projecting into them, to protect a patient or practitioner from unintentional needle sticks, and to protect the needle tips from breakage or contamination. In the embodiment shown, the cradle needle holes 120 are blind; in other embodiments they may be open through to the second side 106 of the cradle 100.

The system 10 may be manufactured in a variety of sizes and/or shapes to meet the needs of various patients and procedures. For example, a larger system may be used to treat a limb or torso, while a smaller system may be used to treat an ear or a small skin flap. A larger sized system may be used in order to accommodate more needles for infusion and/or leeching. The shape of the housing and/or base may be optimized to fit a particular body part; for example the base second side may be concavely curved to fit around the curve of a limb or digit. In one exemplary embodiment, the fluid exchange assembly 15 may have a height of 6 mm and a diameter of 25 mm. The compact size of the fluid exchange assembly 15 may meet a previously unmet need of patient convenience and portability. The compact size may allow a patient to comfortably and unobtrusively carry the attached fluid exchange assembly 15 attached to the target tissue site between treatments.

The fluid exchange assembly 15 may beneficially include no moving parts; thus there may be no issues associated with moving parts while the fluid exchange assembly 15 is being stored, transported or carried on the patient. For example, there no possibility of moving parts coming out of adjustment or alignment with one another, no possibility of moving parts being lost, and no possibility of the system 10 unintentionally being activated. The system 10 may be described as being passive, and may therefore be connected to an external activator such as a peristaltic pump to engage in fluid exchange.

It will be appreciated by a person of skill in the art that in other embodiments of the invention, the inflow and outflow pathways may be reversed. Thus, blood and other fluids may be routed through the inflow pathway of the system 10, and heparin or other fluids may flow through the outflow pathway(s) of the system 10. In addition, the number, arrangement and location of needles, ports, needle holes, channels and passages can vary. For example, one embodiment may include one inflow needle and pathway, and one outflow needle and pathway. Another embodiment may include one inflow needle and pathway, and two or more outflow needles and pathways. One or more needles may feed into a single inflow or outflow pathway. Each needle may be situated at an entrance port of a channel, and the entrance ports may all be equidistant from the exit port of the channel.

The channel housing 20, base 50, and cradle 100 may be manufactured from one or more biocompatible polymer(s) by a 3D printing process. Alternatively, they may be formed by plastic molding, machining, stamping, die casting, and/or any other manufacturing method known in the art. One example of a suitable biocompatible polymer includes PolyJet photopolymer (MED610) supplied by Stratasys™. The gasket may be a silicone membrane as disclosed herein; in alternative embodiments, another material may be used to form the gasket between the base and housing, or no gasket may be used. In another embodiment (not shown), the inflow and outflow pathways may be formed entirely within a gasket, which may be sandwiched between a housing and the base for support in a manner similar to that of the membrane 42. Inner and/or outer surfaces of the system 10 may be coated. For example, all or part of the inflow or outflow pathway(s) may be coated with an antithrombotic material, and/or a hydrophobic material to promote fluid flow and reduce friction. The base second side 64, which may contact skin or tissue, may be coated with a hypoallergenic material.

An anticoagulant such as heparin may be supplied and infused through the inflow pathway as described herein. One or more other treatment agents may be supplied in combination with, or in place of, the anticoagulant. Treatment agents may include analgesics, local anesthetics, anti-inflammatories, antiseptics, anesthetics, antihistamines, antibiotics, antithrombotics and/or vasodilator fluids, and combinations thereof, among others.

The system 10 may be provided as a modular system in a kit, or toolbox. A kit may include variously sized and shaped fluid exchange assemblies 15 and cradles 100, to allow the practitioner to select the appropriately sized and/or shaped assembly 15 for the body part or tissue to be treated. A kit may include variously sized and shaped housings 20, gaskets 42, bases 50, needles, and/or cradles 100.

Figure 9:
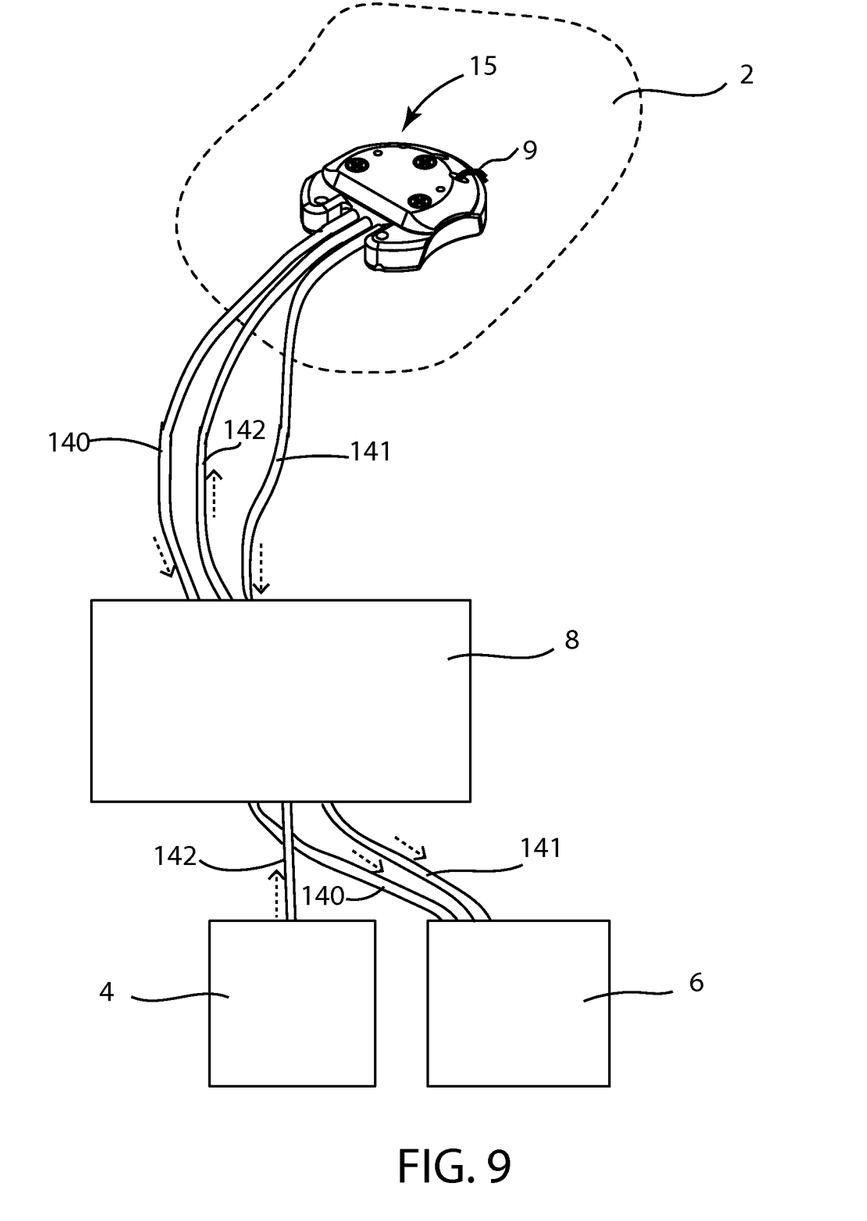
FIG. 9 is a schematic diagram of the fluid exchange assembly of FIG. 7 attached to a patient's tissue, and inflow and outflow tubing connecting the fluid exchange assembly to a peristaltic pump, a treatment agent source, and a reservoir, with dashed arrows showing the directions of flows of fluids into and out of the fluid exchange assembly.

Referring to FIGS. 7A, 7B and 9, in a method of use, the system 10 may be removed from sterile packaging. The patient's skin, skin flap, and/or other target area of treatment 2 may be prepared. A first end of an inflow tube 142 may be connected to the inflow entrance passage 72; the inflow tube first end may be inserted partially into the inflow entrance passage 72. A second end of the inflow tube 142 may be connected to a supply of heparin or other fluid treatment agent 4. The outflow tubes 140, 141 may be similarly connected to the outflow exit passages 80, 90. The second ends of the outflow tubes 140, 141 may be connected to a reservoir 6 for capturing fluid leeched out of the patient. The inflow tube 142 and the outflow tubes 140, 141 may be connected to a pumping device such as a peristaltic pump 8. The inflow tube 142 and the outflow tubes 140, 141 may be connected to the peristaltic pump 8 such that the pumping action of the peristaltic pump 8 causes fluid in the inflow tube 142 to flow in a first direction, and the fluid in the outflow tubes 140, 141 to flow in the opposite direction from the first direction, as seen in FIG. 9. Alternatively, the inflow tube 142 and the outflow tubes 140, 141 tubes may be connected to the peristaltic pump 8 individually in sequence, so that infusion is followed by fluid leeching, or vice versa. If desired, only inflow tube 142 or the outflow tubes 140, 141 may be connected to the peristaltic pump 8, so that either infusion or leeching occurs.

The fluid exchange assembly 15 may be detached from cradle 100, and the fluid exchange assembly 15 may be attached to the patient with the needles 130, 131, 132 penetrating into the targeted area of treatment 2. One or more sutures 9 may be routed through the securement passages 40, 96, and the fluid exchange assembly 15 may be secured to the patient's skin or other tissue. In addition to the suture(s) or as an alternative, an adhesive such as surgical tape may be used to secure the fluid exchange assembly 15 to the patient. The peristaltic pump 8 may be activated to begin pumping. As pumping occurs, heparin or another fluid treatment agent may be urged from the supply 4 and infused into the patient along the inflow pathway 74. Blood and/or other accumulated fluids may be suctioned from the patient along the outflow pathways 84, 94 and into the reservoir 6. When a desired amount of fluid inflow and outflow has occurred, the peristaltic pump 8 may be turned off, the inflow and outflow tubes 142, 140, 141 may be removed from the inflow entrance passage 72 and outflow exit passages 80, 90, and the inflow and outflow tubes 142, 140, 141 may be removed from the peristaltic pump 8.

After cessation of leeching and/or infusion, and removal of the inflow and outflow tubes 142, 140, 141 from the fluid exchange assembly 15, the patient may continue to carry the fluid exchange assembly 15. For example, a practitioner may prescribe several leeching treatments, dispersed over a sequence of 3 to 7 days. Once the fluid exchange assembly 15 is attached to the patient, it may stay attached to the patient for the entire sequence of days until all leeching treatments are completed. When it is time for a leeching treatment, a practitioner may simply attach the inflow and outflow tubes 142, 140, 141 and engage the peristaltic pump 8 to perform the treatment. The size and low profile of the fluid exchange assembly 15 may make it feasible and reasonable for the patient to carry the fluid exchange assembly 15 between treatments. This is in contrast to other fluid removal systems in which fluid exchange is carried out by an assembly that includes a pump. In such a case, the pump must be carried by the patient between treatments, or the patient must be entirely detached from the fluid removal system between treatments.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. §112 Para. 6. It will be apparent to those having skill in the art that changes may be made to the details of the above-described embodiments without departing from the underlying principles of the invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

What is claimed is:

1. A system for promoting fluid exchange within a target tissue area, the system comprising:
   a first needle comprising a first lumen sized to receive blood from target tissue area;
   a second needle comprising a second lumen sized to receive blood from the target tissue area; and
   a housing comprising:
      a first outflow channel comprising a first branch, a second branch, and an exit branch in fluid communication with the first branch and the second branch, wherein the exit branch is intermediate the first branch and the second branch, and wherein the exit branch is orthogonal to the first needle and the second needle;
      an outflow exit port in fluid communication with the exit branch;
      a first outflow entrance port in fluid communication with the first branch;
      a second outflow entrance port spaced apart from the first outflow entrance port and in fluid communication with the second branch;
   wherein the first needle and the second needle are coupled to the first outflow entrance port and the second outflow entrance port, respectively, such that blood flows from the first lumen into the first branch and from the second lumen into the second branch; and
   wherein the first outflow channel is shaped to promote laminar flow of blood from the first outflow entrance port and the second outflow entrance port to the outflow exit port.

2. The system of claim 1, wherein the first branch comprises, along a majority of the first branch length, a first cross-sectional area, the second branch comprises, along a majority the second branch length, a second cross-sectional area, and the exit branch comprises, along a majority the exit branch length, an exit cross-sectional area;
   wherein the first cross-sectional area is equal to the second cross-sectional area; and
   wherein the exit cross-sectional area is equal to the sum of the first cross-sectional area and the second cross-sectional area.

3. The system of claim 1, wherein the first branch and the second branch are equal in length.

4. The system of claim 1, wherein the first branch, the second branch, and the exit branch cooperate to define a T-shape.

5. The system of claim 1, further comprising:
   a third needle comprising a third lumen;
   wherein the housing further comprises:
      an inflow channel; and
      an inflow exit port in fluid communication with the inflow channel;
   wherein the third needle is coupled to the inflow exit port to permit fluid to flow from the inflow channel into the third lumen.

6. The system of claim 1, wherein the system further comprises:
   a fourth needle comprising a fourth lumen sized to receive blood from the target tissue area;
   a fifth needle having a fifth lumen sized to receive blood from the target tissue area; and
   wherein the housing further comprises:
      a second outflow channel comprising a second outflow channel first branch, a second outflow channel second branch, and a second outflow channel exit branch in fluid communication with the second outflow channel first branch and the second outflow channel second branch;
      a second outflow channel outflow exit port in fluid communication with the second outflow channel exit branch;
      a second outflow channel first outflow entrance port in fluid communication with the second outflow channel first branch;
      a second outflow channel second outflow entrance port spaced apart from the second outflow channel first outflow entrance port and in fluid communication with the second outflow channel second branch;
   wherein the fourth needle and the fifth needle are coupled to the second outflow channel first outflow entrance port and the second outflow channel second outflow entrance port, respectively, such that blood flows from the fourth lumen into the second outflow channel first branch and from the fifth lumen into the second outflow channel second branch; and
   wherein the second outflow channel is shaped to promote laminar flow of blood from the second outflow channel first outflow entrance port and the second outflow channel second outflow entrance port to the second outflow channel outflow exit port.

7. The system of claim 1, wherein the housing comprises at least one securement opening sized to receive a suture to secure the housing to the target tissue area.

8. The system of claim 1, further comprising a cradle shaped to retain the housing, wherein the cradle comprises a plurality of openings sized to receive the first needle and the second needle.

9. The system of claim 1, wherein the housing comprises a channel housing coupled to a base, wherein the channel housing comprises the first outflow channel, and the base comprises the first outflow entrance port, the second outflow entrance port, and the outflow exit port.

10. The system of claim 9, further comprising a gasket positioned between the channel housing and the base to restrict fluid leakage from the first outflow channel.

11. A system for promoting fluid exchange within a target tissue area, the system comprising:
    a first needle comprising a first lumen sized to receive blood from target tissue area;
    a second needle comprising a second lumen sized to receive blood from the target tissue area; and
    a housing comprising:
        a first outflow channel comprising a first branch, a second branch, and an exit branch in fluid communication with the first branch and the second branch, wherein the exit branch is intermediate the first branch and the second branch, and wherein the exit branch is orthogonal to the first needle and the second needle;
        an outflow exit port in fluid communication with the first outflow channel;
        a first outflow entrance port in fluid communication with the first outflow channel;
        a second outflow entrance port spaced apart from the first outflow entrance port and in fluid communication with the first outflow channel;
    wherein the first needle and the second needle are coupled to the first outflow entrance port and the second outflow entrance port, respectively, such that blood flows from the first lumen into the first outflow channel and from the second lumen into the first outflow channel;
    wherein the outflow exit port is connectable to an external pump; and
    wherein the housing contains no moving parts.

12. The system of claim 11, further comprising:
    a third needle comprising a third lumen;
    wherein the housing further comprises:
        an inflow channel; and
        an inflow exit port in fluid communication with the inflow channel;
    wherein the third needle is coupled to the inflow exit port to permit fluid to flow from the inflow channel into the third lumen.

13. The system of claim 11, wherein the system further comprises:
    a fourth needle comprising a fourth lumen sized to receive blood from the target tissue area;
    a fifth needle having a fifth lumen sized to receive blood from the target tissue area; and
    wherein the housing further comprises:
        a second outflow channel;
        a second outflow channel outflow exit port in fluid communication with the second outflow channel;
        a second outflow channel first outflow entrance port in fluid communication with the second outflow channel;
        a second outflow channel second outflow entrance port spaced apart from the second outflow channel first outflow entrance port and in fluid communication with the second outflow channel;
    wherein the fourth needle and the fifth needle are coupled to the second outflow channel first outflow entrance port and the second outflow channel second outflow entrance port, respectively, such that blood flows from the fourth lumen into the second outflow channel and from the fifth lumen into the second outflow channel.

14. The system of claim 11, wherein the first outflow channel is shaped to promote laminar flow of blood through the first outflow channel.

15. The system of claim 11, wherein the housing comprises a channel housing coupled to a base, wherein the channel housing comprises the first outflow channel, and the base comprises the first outflow entrance port, the second outflow entrance port, and the outflow exit port.

16. A method for promoting fluid exchange within a target tissue area, the method comprising:
    penetrating the target tissue area with a first needle, a second needle, and a third needle, wherein the first needle, the second needle and third needle are seated in a housing;
    from outside the housing, exerting pressure on blood to draw the blood from the target tissue area through the first needle and the second needle into the housing;
    conducting the blood from the first needle and the second needle into a first outflow channel in the housing;
    conducting the blood out of the housing through a first outflow exit port;
    from outside the housing, exerting pressure on a treatment agent to urge the treatment agent to flow into an inflow channel in the housing, the treatment agent flowing through a first inflow entrance port into the inflow channel;
    conducting the treatment agent through an inflow exit port and into the third needle; and
    conducting the treatment agent from the third needle into the target tissue area, wherein drawing the blood from the target tissue area and urging the treatment agent into the inflow channel are carried out simultaneously.

17. The method of claim 16, further comprising attaching the housing to the target tissue area by passing a suture through a securement opening in the housing and securing the suture to the target tissue area.

18. The method of claim 16, further comprising:
    connecting the first outflow exit port and the first inflow entrance port to a pump external to the housing; and
    activating the pump to exert the pressure on the blood and exert the pressure on the treatment agent.

19. The method of claim 16, further comprising:
    penetrating the target tissue area with a fourth needle and a fifth needle, wherein the fourth needle and the fifth needle are seated in the housing;
    from outside the housing, exerting pressure on the blood to draw the blood from the target tissue area through the fourth needle and the fifth needle into the housing;
    conducting the blood into a second outflow channel in the housing; and
    conducting the blood out of the housing through a second outflow exit port.

* * * * *